(12) United States Patent
Pugh et al.

(10) Patent No.: US 8,665,526 B2
(45) Date of Patent: *Mar. 4, 2014

(54) ARCUATE LIQUID MENISCUS LENS

(75) Inventors: Randall B. Pugh, Jacksonville, FL (US); Daniel B. Otts, Jacksonville, FL (US); Adam Toner, Jacksonville, FL (US); Edward R. Kernick, Jacksonville, FL (US); James Daniel Riall, St. Johns, FL (US); Sharika Snook, St. Augustine, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 281 days.

This patent is subject to a terminal disclaimer.

(21) Appl. No.: 13/095,786

(22) Filed: Apr. 27, 2011

(65) Prior Publication Data

US 2011/0279905 A1 Nov. 17, 2011

Related U.S. Application Data

(60) Provisional application No. 61/334,780, filed on May 14, 2010.

(51) Int. Cl.
*G02B 3/12* (2006.01)
*G02B 1/06* (2006.01)

(52) U.S. Cl.
USPC ................. 359/665; 351/159.34; 351/159.68

(58) Field of Classification Search
CPC .............. G02B 1/06; G02B 3/12; G02B 3/14; G02C 7/04
USPC ................. 359/665–667; 351/159.34, 159.68
See application file for complete search history.

(56) References Cited

U.S. PATENT DOCUMENTS

| 5,071,229 | A  | * | 12/1991 | Oaki et al. ..................... 349/200 |
| 7,311,398 | B2 | * | 12/2007 | Kuiper et al. ............ 351/159.04 |
| 7,327,523 | B2 | * | 2/2008  | Tanaka .......................... 359/665 |
| 7,724,444 | B2 | * | 5/2010  | Kuiper et al. ................. 359/666 |
| 2010/0020285 | A1 | | 1/2010 | Berge |
| 2010/0149651 | A1 | * | 6/2010 | Berge et al. ................... 359/666 |

FOREIGN PATENT DOCUMENTS

| WO | WO 03069380 A1 | 8/2003 |
| WO | WO 2004077125 A2 | 9/2004 |
| WO | WO 2004077125 A3 | 9/2004 |
| WO | WO 2004099844 A1 | 11/2004 |
| WO | WO 2004099845 A1 | 11/2004 |
| WO | WO 2004099846 A1 | 11/2004 |
| WO | WO 2004102253 A1 | 11/2004 |
| WO | WO 2005069043 A1 | 7/2005 |
| WO | WO 2005069044 A1 | 7/2005 |
| WO | WO 2005088388 A1 | 9/2005 |
| WO | WO 2005096029 A1 | 10/2005 |
| WO | WO 2005096030 A1 | 10/2005 |
| WO | WO 2005109074 A1 | 11/2005 |
| WO | WO 2006123288 A2 | 11/2006 |
| WO | WO 2006123288 A3 | 11/2006 |

OTHER PUBLICATIONS

PCT International Search Report, dated Aug. 29, 2011, for PCT Int'l. Appln. No. PCT/US2011/036431.

* cited by examiner

*Primary Examiner* — Darryl J Collins

(57) ABSTRACT

The present invention relates generally to an arcuate liquid meniscus lens, some specific embodiments include a liquid meniscus lens with a front curve arcuate lens and a back curve arcuate lens. Embodiments may also include a lens of suitable size and shape for inclusion in a contact lens.

25 Claims, 5 Drawing Sheets

ARCUATE LIQUID MENISCUS LENS

RELATED APPLICATIONS

This application claims priority to Provisional U.S. Patent Application Ser. No. 61/334,780, filed on May 14, 2010.

FIELD OF USE

The present invention relates generally to an arcuate liquid meniscus lens, some specific embodiments include a liquid meniscus lens with a front curve arcuate lens and a back curve arcuate lens.

BACKGROUND

Liquid meniscus lenses have been known in various industries. As discussed more fully below with reference to FIGS. 1A and 1B, known liquid meniscus lenses were engineered in cylindrical shapes with a perimeter surface formed by points at a fixed distance from an axis which is a straight line. Known liquid meniscus lenses have been limited to designs with a first interior surface generally parallel to second interior surface and each perpendicular to a cylindrical axis. Known examples of the use of liquid meniscus lenses include devices such as electronic cameras and mobile phone devices.

Traditionally, an ophthalmic device, such as a contact lens and an intraocular lens included a biocompatible device with a corrective, cosmetic or therapeutic quality. A contact lens, for example, can provide one or more of: vision correcting functionality; cosmetic enhancement; and therapeutic effects. Each function is provided by a physical characteristic of the lens. A design incorporating a refractive quality into a lens can provide a vision corrective function. A pigment incorporated into the lens can provide a cosmetic enhancement. An active agent incorporated into a lens can provide a therapeutic functionality.

More recently, it has been theorized that electronic components may be incorporated into a contact lens. Some components can include semiconductor devices. However, physical constraints including the size, shape and control aspects of a liquid meniscus lens have precluded their use in an ophthalmic lens. Generally the cylindrical shape, sometimes referred to as the "hockey puck" shape of liquid meniscus lenses, has not been conducive to something that can work in a human eye. Other curved lenses have only been theoretical and do not provide a realistic design for ophthalmic use.

SUMMARY

Accordingly, the present invention provides a liquid meniscus lens with physical features conducive for inclusion in an ophthalmic lens, such as a contact lens or an intraocular lens.

According to the present invention, a first arcuate shaped optic is proximate to a second arcuate shaped optic with a cavity formed therebetween. A saline solution and an oil are maintained within the cavity. Application of electrical charge to a perimeter area of one or both of the first arcuate optic and the second arcuate optic changes the physical shape of a meniscus formed between the saline solution and oil maintained within the cavity.

DETAILED DESCRIPTION OF THE INVENTION

The present invention provides for a liquid meniscus lens with at least one of a front curve lens and a back curve lens defining a meniscus cavity of the liquid meniscus lens.

Figure 1A:
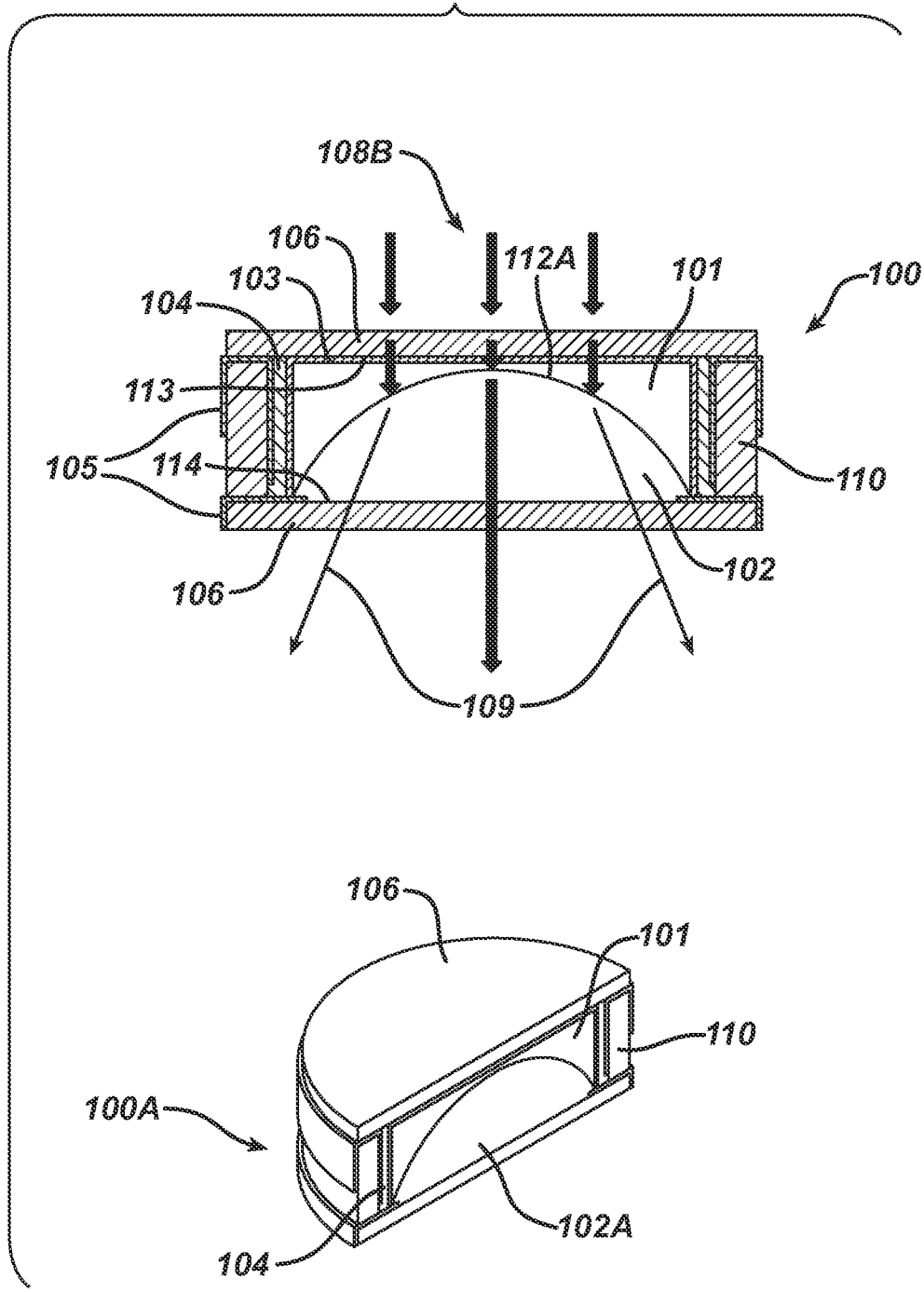
FIG. 1A illustrates a prior art example of a cylindrical liquid meniscus lens in a first state.

Referring now to FIG. 1A, a cut away view of a prior art lens 100 is illustrated with an oil 101 and a salt water solution 102 contained within cylinder 110. The cylinder 110 includes two plates of optical material 106. Each plate 106 includes a flat interior surface 113-114. The cylinder 110 includes an interior surface that is essentially rotationally symmetric. In some prior art embodiments, one or more surfaces may include a hydrophobic coating. Electrodes 105 are also included on or about the perimeter of the cylinder. An electrical insulator may also be used proximate to the electrodes 105.

According to the prior art, each of the interior surfaces 113-114 is essentially flat or planar. An interface surface 112A is defined between the salt water 102A and the oil 101. As illustrated in FIG. 1A, the shape of the interface 112A is combined with the refractive index properties of the salt water 102A and the oil 101 to receive incident light 108 through a first interior surface 113 and provide divergent light 109 through a second interior surface 113. The shape of the interface surface between the oil 101 and the salt water 102 may be altered with the application of an electrical current to the electrodes 105.

FIG. 100A illustrates a perspective view of the prior art lens illustrated at 100.

Figure 1B:
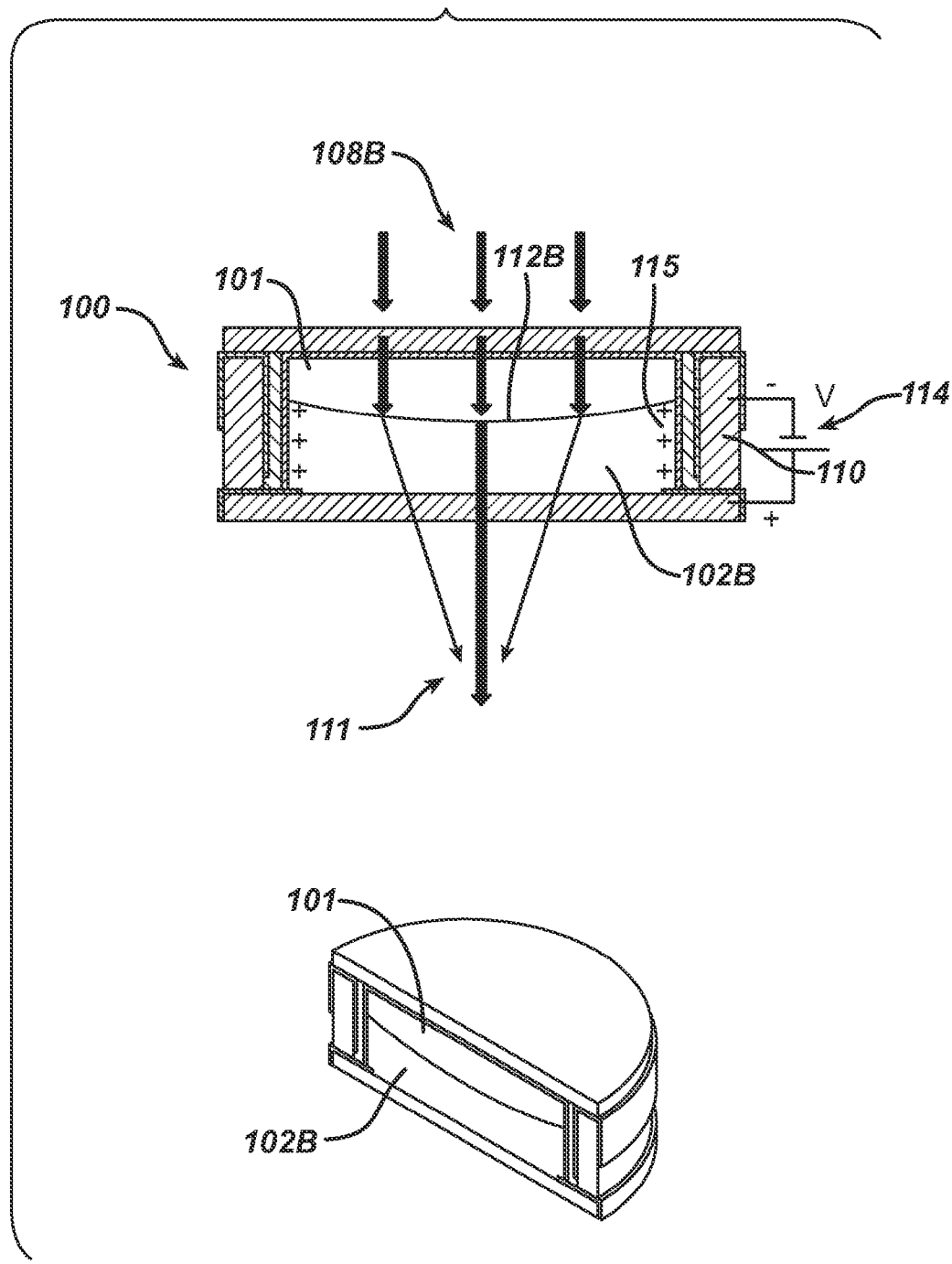
FIG. 1B illustrates the prior art example of a cylindrical liquid meniscus lens in a second state.

Referring now to FIG. 1B, the prior art lens 100 is illustrated in an energized state. The energized state is accomplished by applying voltage 114 across the electrodes 105. The shape of the interface surface 112B between the oil 101 and the salt water 102 is altered with the application of an electrical current to the electrodes 105. As illustrated in FIG. 1B, incident light 108B passing through the oil 101 and the salt water 102B is focused into a convergent light pattern 111.

Figure 2:
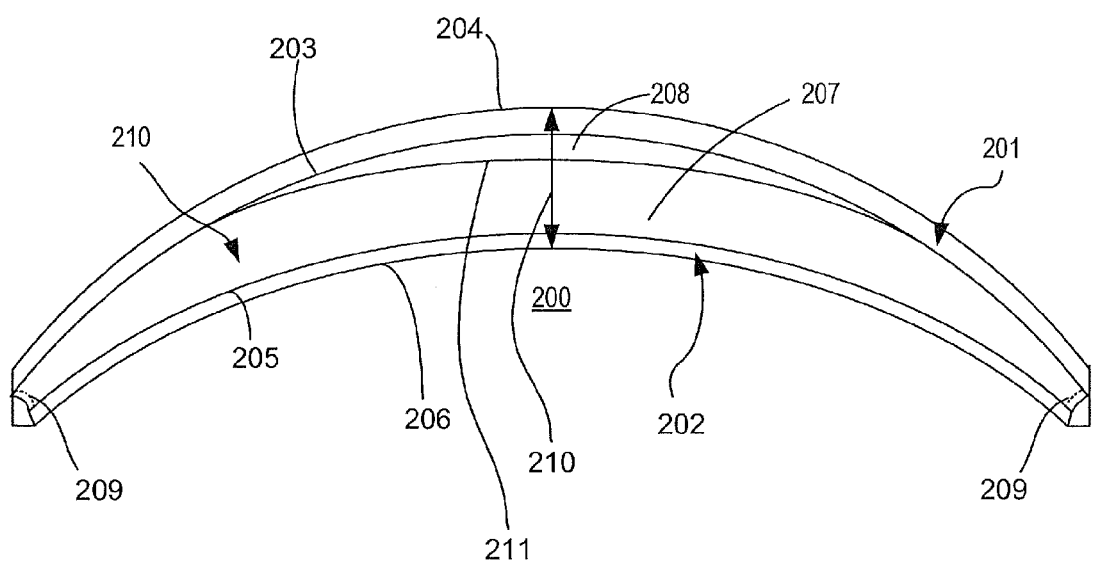
FIG. 2 illustrates a profile sliced cut away of an exemplary liquid meniscus lens according to some embodiments of the present invention.

Referring now to FIG. 2, a cut away view of a liquid meniscus lens 200 with a front curve lens 201 and a back curve lens 202. The front curve lens 201 and the back curve lens 202 are positioned proximate to each other and form a cavity 210 therebetween. The front curve lens includes a concave arcuate interior lens surface 203 and a convex arcuate exterior lens surface 204. The concave arcuate lens surface 203 may have one or more coatings (not illustrated in FIG. 2). Coatings may include, for example, one or more of electrically conductive materials or electrically insulating materials, hydrophobic materials or hydrophilic materials. One or both of the arcuate lens surface 203 and the coatings are in liquid and optical communication with an oil 208 contained within the cavity 210.

The back curve lens 202 includes a convex arcuate interior lens surface 205 and a concave arcuate exterior lens surface 205. The convex arcuate lens surface 205 may have one or more coatings (not illustrated in FIG. 2). Coatings may include, for example, one or more of electrically conductive materials or electrically insulating materials, hydrophobic materials or hydrophilic materials. At least one of the convex arcuate lens surface 205 and the coatings are in liquid and optical communication with a saline solution 207 contained within the cavity 210. The saline solution 207 includes one or more salts or other components which are electrically conductive and as such may be either attracted to or repulsed by an electric charge.

According to the present invention, an electrically conductive coating 209 is located along at least a portion of a periphery of one or both of the front curve lens 201 and the back curve lens 202. The electrically conductive coating 209 may include gold or silver and is preferably biocompatible. Application of an electrical charge to the electrically conductive coating 209 creates either an attraction or a repulsion of the electrically conductive salts or other components in the saline solution.

The front curve lens 201 has an optical power in relation to light passing through the concave arcuate interior lens surface 203 and a convex arcuate exterior lens surface 204. The optical power may be 0 or may be a plus or minus power. In some preferred embodiments, the optical power is a power typically found in corrective contact lenses, such as, by way of non-limiting example, a power between −8.0 and +8.0 diopters.

The back curve lens 202 has an optical power in relation to light passing through the convex arcuate interior lens surface 205 and a concave arcuate exterior lens surface 206. The optical power may be 0 or may be a plus or minus power. In some embodiments, the optical power is a power typically found in corrective contact lenses, such as, by way of non-limiting example, a power between −8.0 and +8.0 diopters.

Various embodiments may also include a change in optical power associated with a change in shape of a liquid meniscus 211 formed between the saline solution 207 and the oil. In some embodiments, a change in optical power may be relatively small, such as, for example, a change of between 0 to 2.0 diopters of change. In other embodiments, a change in optical power associated with a change in shape of a liquid meniscus may be up to about 30 or more diopters of change. Generally, a higher change in optical power associated with a change in shape of a liquid meniscus 211 is associated with a relatively thicker lens thickness 210.

According to some embodiments of the present invention, such as those embodiments that may be included in an ophthalmic lens, such as a contact lens, a cross cut lens thickness 210 of an arcuate liquid meniscus lens 200 will be up to about 1,000 microns thick. An exemplary lens thickness 210 of a relatively thinner lens 200 may be up to about 200 microns thick. Preferred embodiments may include a liquid meniscus lens 200 with a lens thickness 210 of about 600 microns thick. Generally a cross cut thickness of front curve lens 201 may be between about 35 microns to about 200 microns and a cross cut thickness of a back curve lens 202 may also be between about 35 microns and 200 microns.

According to the present invention, an aggregate optical power is an aggregate of optical powers of the front curve lens 201 the back curve lens 202 and a liquid meniscus 211 formed between the oil 208 and the saline solution 207. In some embodiments, an optical power of the lens 200 will also include a difference in refractive index as between one or more of the front curve lens 201, the back curve lens 202, oil 208 and the saline solution 207.

In those embodiments that include an arcuate liquid meniscus lens 200 incorporated into a contact lens, it is additionally desirous for the saline 207 and oil 208 to remain stable in their relative positions within the curved liquid meniscus lens 200 as a contact wearer moves. Generally, it is preferred to prevent the oil 208 from floating and moving relative to the saline 207 when the wearer moves, accordingly, an oil 208 and saline solution 207 combination is preferably selected with a same or similar density. Additionally, an oil 208 and a saline solution 207 preferably have relatively low immiscibility so that the saline 207 and oil 208 will not mix.

In some preferred embodiments, a volume of saline solution contained within the cavity is greater than the volume of oil contained within the cavity. Additionally, some preferred embodiments include the saline solution 207 in contact with essentially an entirety of an interior surface 205 of the back curve lens 200. Some embodiments may include a volume of oil 208 that is about 66% or more by volume as compared to an amount of saline solution 207. Some additional embodiments may include an arcuate liquid meniscus lens wherein a volume of oil 208 that is about 90% or less by volume as compared to an amount of saline solution 207.

Figure 3:
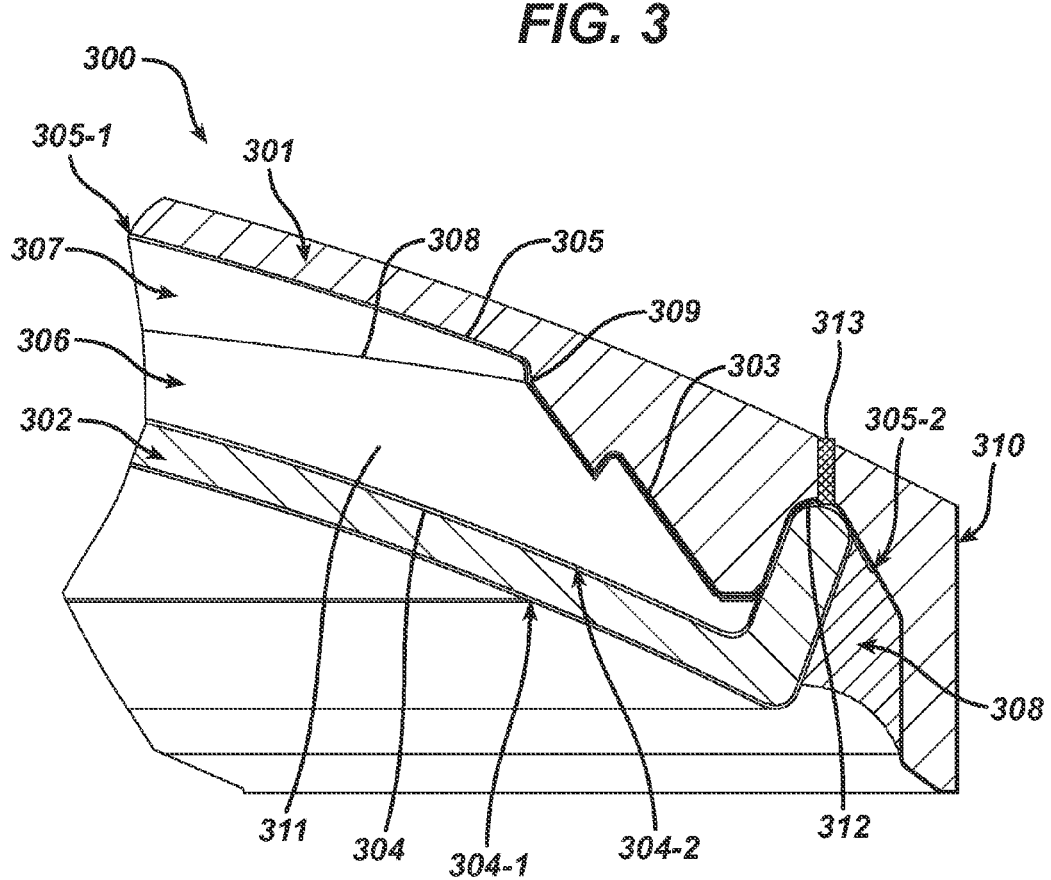
FIG. 3 illustrates a cross section of a portion of an exemplary arcuate liquid meniscus lens, according to some embodiments of the present invention.

Referring now to FIG. 3, a cutaway of an edge portion arcuate liquid meniscus lens 300 is illustrated. As discussed above, an arcuate liquid meniscus lens 300 includes combined front curve lens 301 and back curve lens 302 components. The front curve lens 301 and back curve lens 302 may be formed with one or more materials that are at least partially transparent. In some embodiments, one or both of the front curve lens 301 and the back curve lens 302 include generally optically clear plastic, such as for example, one or more of: PMMA, Zeonor and TPX.

One or both of the front curve lens 301 and the back curve lens may be fashioned, for example via processes such as one or more of: single point diamond turning lathing; injection molding; digital mirror device free forming.

One or both of the front curve lens 301 and the back curve lens 302 may include a conductive coating 303, as illustrated, the conductive coating 303 extending along a perimeter portion from 309 to 310. In some preferred embodiments, a conductive coating 303 includes gold. The gold may be applied via a sputter process, vapor deposition or other known process. Alternative conductive coating 303 may include, by way of non-limiting example, aluminum, nickel, and indium tin oxide. Generally, the conductive coating 303 will be applied to perimeter areas of one or both of the front curve lens 301 and the back curve lens c 302.

In some embodiments, of the present invention, a back curve lens 302 has a conductive coating 304 applied to specific areas. For example, portions about the perimeter of the back curve lens 302 may be coated from a first boundary 304-1 to a second boundary 304-2. The gold coatings may be applied for example via a sputter process or a vapor deposition. In some embodiments, a mask may be used to apply the gold or other conductive material in a predetermined pattern around one or more perimeter portions of a front curve lens 301 or a back curve lens 302. Alternative conductive materials may be applied using various methods and covering varying areas of the back curve lens 302.

In some embodiments, a conductive pass through, such as, for example one or more holes or slots in a back curve lens 302 may be filled with a conductive filler material, such as, for example, a conductive epoxy. The conductive filler may provide electrical communication to a conductive coating on an interior surface of one or both of the front curve lens 301 and the back curve lens 302.

In another aspect of the present invention, one or both of the front curve lens 301 and the back curve lens 302 may be created from multiple different materials wherein an optical zone generally in a central area of the front curve lens 301 and the back curve lens 302 (not illustrated) may include an optically transparent material and a peripheral zone may include an optically opaque area that includes an electrically conductive material. The optically opaque area may also include one or more of control circuitry and energy sources.

In still another aspect, in some embodiments, an insulator coating 305 is applied to a front curve lens 301. By way of non-limiting example, the insulator coating 305 may be applied in an area from a first region 305-1 and extend to a second region 305-2. Insulators may include, for example, Parylene C, Teflon AF or other materials with various electrical and mechanical characteristics and electrical resistance.

In some specific embodiments, an insulator coating 305 creates a boundary area to maintain separation between the conductive coating 303 and a saline solution 306 contained in a cavity between the front curve lens 301 and the back curve lens 302. Some embodiments accordingly include an insulator coating 305 patterned and positioned in an one or more areas of one or both of the front curve lens 301 and the back curve lens 302 to prevent a positively charged conductor 303 and negatively charged saline solution 306 from coming into contact, wherein contact of a conductor 303 and a saline solution 306 will result in an electrical short. Embodiments may include a positively charged saline solution 306 and a negatively charged conductor 303.

Still other embodiments may allow for a short between a conductor 303 and a saline solution 306 as a reset function of circuitry associated with the operation of the lens 300. For example, a short condition may interrupt power source to the lens and cause the saline solution 306 and the oil 307 to revert to a default position.

Some preferred embodiments include a conductor 303 that extends from an area 309 on the interior of the cavity 311 to an area 310 external to the cavity 311. Other embodiments may include a channel 312 through the front curve lens or the back curve lens which may be filled with a conductive material 313, such as, for example, a waterproof conductive epoxy. The conductive material 313 may form or be connected to an electrical terminal external to the cavity. An electrical charge may be applied to the terminal and conducted to the coating via the conductive material 313 in the channel 312.

The thickness of the insulator coating 305 may be varied as a parameter of lens performance. According to the present invention, charged components, including the saline solution 306 and the conductor 303, are generally maintained on either side of the insulator coating 305. The present invention provides for an indirect relationship between the thickness of the insulator coating 305 and an electrical field between the saline solution 306 and the conductor 303, wherein the farther apart the saline solution 306 and the conductor 303 are maintained, the weaker the electrical field will be.

Generally, the present invention provides that electrical field strength may fall off dramatically as insulator coating 305 thickness increases. The closer together the fields are, the more energy that will generally be available to move a spherical liquid meniscus boundary 308. As a distance between the saline solution 306 and conductor 303 increases, the farther apart electrical fields of the saline solution 306 and the conductor coating 303 will be and therefore the harder it is to get the spherical meniscus boundary 308 to move. Inversely, the thinner the insulator coating 305, the more sensitive movement of the spherical liquid meniscus 308 is to defects in an insulator coating 305. Generally, even a relatively small hole in the insulator coating 305 will short a lens 300 out.

In some embodiments, it is desirable to include a saline solution 306 with density that is generally the same density of an oil 307 also contained within the lens 300. For example, a saline solution 306 may preferably include a density that is within 10% of a density of an oil 307 and more preferably the saline solution 306 will include a density within 5% of a density of an oil and most preferably within about 1%. In some embodiments, a concentration of salts or other components within the saline solution 306 may be adjusted to adjust the density of the saline solution 306.

According to the present invention, an arcuate liquid meniscus lens 300 will provide a more stable optical quality by limiting movement of the oil 307 in relation to the front curve lens 301 and the back curve lens 302. One method of maintaining stability of movement of the oil 307 in relation to one or both of the arcuate front curve lens 301 and the back curve lens 302 is to maintain a relatively congruent density in the oil 307 and the saline solution 306. In addition, due to the curve design of the interior surfaces of both the front curve lens 301 and the back curve lens 302, the relative depth or thickness of a layer of saline solution 306 is diminished as compared to a traditional cylindrical lens design. Accordingly, stability of a position of oil within the lens 300 becomes more in order to avoid movement of the oil and possible breaking of the meniscus between the oil 306 and the saline solution 307.

In some preferred embodiments, the saline solution 306 provides a low refractive index as compared to the oil 307 which provides a relatively high refractive index. However, in some embodiments it is possible to include a saline solution 306 with a higher refractive index as compared to the oil 307 which in such cases provides a relatively lower refractive index.

An adhesive 308 may be used to secure the front curve lens 301 and back curve lens 302 in place proximate to each other thereby retaining the oil 307 and saline solution 306 therebetween. The adhesive 308 acts as a seal so that there is no leakage of saline 306 or oil 307 from the curved liquid meniscus lens 300.

Figure 4:
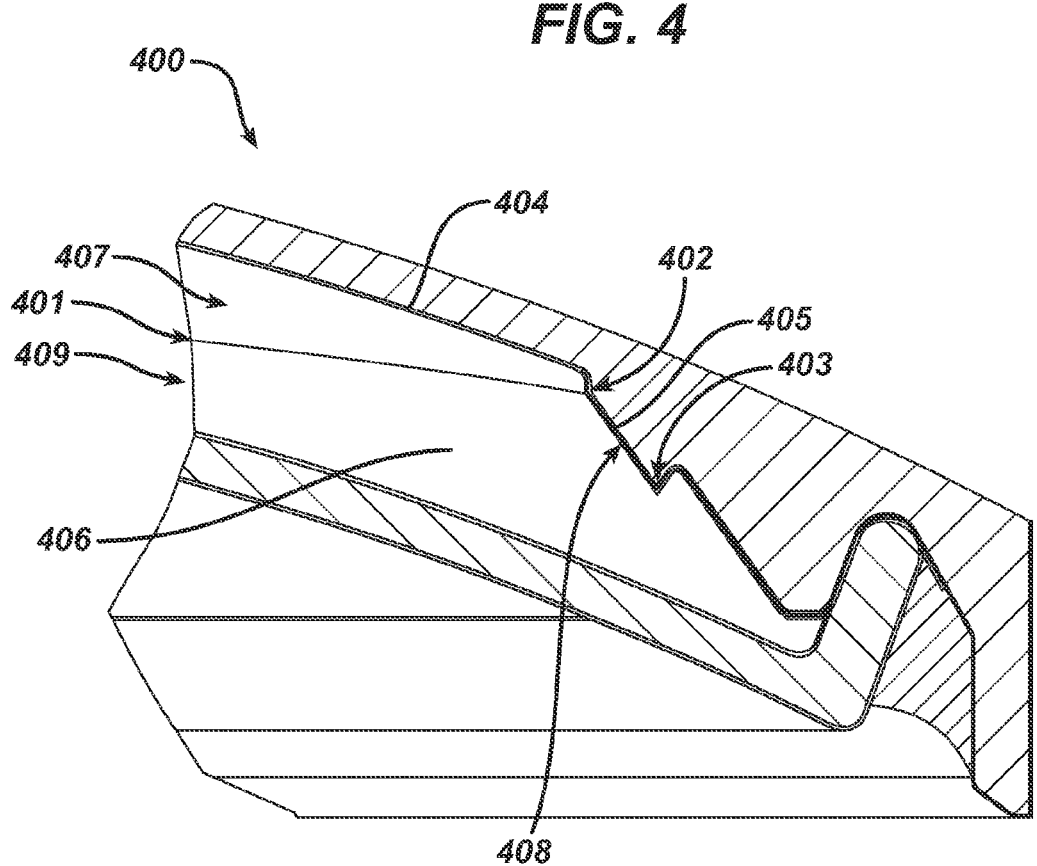
FIG. 4 illustrates additional exemplary aspects of an arcuate liquid meniscus lens.

Referring now to FIG. 4, a curved liquid meniscus lens 400 is illustrated with a liquid meniscus boundary 401 between the saline solution 406 and oil 407. According to some preferred embodiments, a meniscus wall 405 is defined in the front curve lens 404 by a first angular break in an arcuate wall extending between 402 and 403. The liquid meniscus boundary 401 will move up and down the meniscus wall 405 as charge is applied and removed along one or more conductive coatings or conductive materials 408.

In some preferred embodiments, a conductive coating 403 will extend from an area internal to the cavity 409 holding the saline solution 406 and the oil 407 to an area external to the cavity 409 containing the saline solution 406 and oil 407. In such embodiments, the conductive coating 403 may be a conduit of an electrical charge applied to the conductive coating 403 at a point external to the cavity 409 to an area of the conductive coating within the cavity and in contact with the saline solution 406.

The invention claimed is:

1. An optical lens comprising:
   a front curve lens comprising a front curve lens exterior surface and a front curve lens interior surface, wherein both said front curve lens exterior surface and said front curve lens interior surface comprise an arcuate shape;

a back curve lens comprising a back curve lens interior surface and a back curve lens exterior surface, wherein both said back curve lens interior surface and the back curve lens exterior surface comprise an arcuate shape, said back curve lens positioned proximate to said front curve lens such that said front curve lens interior surface and said back curve lens interior surface form a cavity therebetween;

a conductive coating on a portion of said front curve lens interior surface said portion including a perimeter area of said front curve lens interior surface; and an adhesive securing said front curve lens in the position proximate to the back curve lens; and additionally comprising a channel through one or both of the front curve lens and the back curve lens; and a conductive material filling the channel.

2. The optical lens of claim 1 additionally comprising a terminal in electrical communication with the conductive material filling the channel.

3. The optical lens of claim 2 wherein application of an electrical charge to the terminal causes a change in the shape of the meniscus.

4. The optical lens of claim 1 additionally comprising a volume of oil and a volume of saline solution contained within the cavity and a meniscus formed between the oil and saline solution.

5. The optical lens of claim 4 wherein the volume of oil is less than the volume of saline solution contained within the cavity.

6. The optical lens of claim 5 wherein the volume of oil comprises about 66% or greater as compared to the volume of saline solution.

7. The optical lens of claim 5 wherein the volume of oil comprises about 90% or less compared to the volume of saline solution.

8. The optical lens of claim 5 wherein the front curve lens exterior surface comprises an optical power other than about 0.

9. The optical lens of claim 5 wherein the front curve lens interior surface comprises an optical power other than about 0.

10. The optical lens of claim 5 wherein the back curve lens exterior surface comprises an optical power other than about 0.

11. The optical lens of claim 5 wherein the back curve lens interior surface comprises an optical power other than about 0.

12. The optical lens of claim 5 additionally comprising an insulator coating along at least a portion of the interior surface of the front curve lens, wherein the insulator coating comprises an electrical insulator.

13. The optical lens of claim 12, wherein the insulator comprises one of Parylene™ C and Teflon® AF.

14. The optical lens of claim 12 wherein the insulator comprises a boundary area to maintain separation between the conductive coating and a saline solution contained in the cavity between the front curve lens and the back curve lens.

15. The optical lens of claim 4 wherein the volume of oil comprises a density about equal to a density of the saline solution.

16. The optical lens of claim 4 wherein the volume of oil comprises density within about 10% of a density of the saline solution.

17. The optical lens of claim 4 wherein the volume of oil comprises density within about 5% of a density of the saline solution.

18. The optical lens of claim 4 wherein the conductive coating extends from an area interior to the cavity to an area external to the cavity.

19. The optical lens of claim 18, wherein the area of conductive coating external to the cavity forms an electrical terminal for providing an electrical charge to the liquid meniscus lens.

20. The optical lens of claim 18 wherein the saline solution and the oil form a meniscus and an application of an electrical charge to the area of conductive coating external to the cavity causes a change in the shape of the meniscus.

21. The optical lens of claim 18 wherein the electrical charge comprises a direct current.

22. The optical lens of claim 18 wherein the electrical charge comprises about 20.0 volts.

23. The optical lens of claim 18 wherein the electrical charge comprises between about 18.0 volts to 22.0 volts.

24. The optical lens of claim 18 wherein the electrical charge comprises about 5.0 volts.

25. The optical lens of claim 18 wherein the electrical charge comprises between about 3.5 volts to about 7.5 volts.

* * * * *